United States Patent [19]
Paul

[11] 3,935,115
[45] Jan. 27, 1976

[54] COOLANT FOR ROTARY ENGINE
[75] Inventor: George A. Paul, Midland, Mich.
[73] Assignee: The Dow Chemical Company, Midland, Mich.
[22] Filed: Oct. 4, 1973
[21] Appl. No.: 403,705

[52] U.S. Cl. .................................. 252/73; 252/70
[51] Int. Cl.² ........................................ C09K 5/00
[58] Field of Search ............................ 252/73, 70

[56] References Cited
UNITED STATES PATENTS
3,743,452    7/1973    Steinwart .......................... 123/41.1

OTHER PUBLICATIONS
Miller, James E., "Methoxy Propanol Automotive Antifreeze," Soap & Chemical Specialties, Oct. 1967, pp. 68–76 and 212–213.

Primary Examiner—Benjamin R. Padgett
Assistant Examiner—Deborah L. Kyle
Attorney, Agent, or Firm—Ralph M. Mellom; Chessie E. Rehberg

[57] ABSTRACT
An aqueous solution of propylene glycol monomethyl ether is a more effective coolant for rotary (Wankel) engines and less toxic than is gaseous alkylene glycol.

2 Claims, No Drawings

COOLANT FOR ROTARY ENGINE

BACKGROUND OF THE INVENTION

Aqueous solutions of propylene glycol monomethyl ether have been suggested for general use as coolants for internal combustion engines and have been sold commercially for such use in heavy piston-type engines such as are used in buses and heavy trucks but have not been found commercially acceptable for use in automobile engines.

Wankel engines, herein referred to generically as rotary engines, have peculiar coolant problems in that the rotor housing is asymmetrically heated "hot spots" are formed on the combustion side and as a result in extreme cases, severe engine damage can occur. The danger arising from high metal temperatures is made more acute by the fact that as hot spots develop there is often a tendency for solid deposits to form on the coolant side, which deposits further reduce heat transfer, thus aggravating the problem. It is accordingly highly desirable to prevent even transient formation of hot spots under severe conditions, such as high speed, heavy load, rapid acceleration, etc.

While water is the most readily available and effective coolant, antifreeze additives are necessary for cold weather use. Ethylene glycol is by far the most widely used antifreeze additive. It is less efficient than water but more efficient than propylene glycol and similar materials.

There is increasing concern about the use of ethylene glycol because of its high toxicity. Propylene glycol and its ethers are much less toxic than the corresponding ethylene compounds.

In most areas glycol antifreeze is used at a concentration of about 50–60% by weight. However, because of the common habit of adding additional concentrate from time to time to assure that a safe concentration of both antifreeze and corrosion inhibitors is present, it is not unusual to find autos carry antifreeze concentractions of 70% or more. Since the heat transfer efficiency of the fluid decreases as the concentration of antifreeze additive increases, such high concentrations are conducive to the formation of hot spots where metal temperatures are beyond the safe range.

In view of the above problems, it is an object of the present invention to provide a coolant for rotary engines that adquately protects against freezing and also against excessively hot spots on the combustion chamber wall when operating the engine under severe conditions and which has low animal and human toxicity.

SUMMARY OF THE INVENTION

Liquid-cooled rotary engines are effectively cooled by use of an aqueous solution of propylene glycol monomethly ether. Such a solution is more efficient and less toxic than is a solution of ethylene glycol. Suitable concentrations are essentially those used with ethylene glycol and depend primarily on the lowest temperatures that are to be expected.

DETAILED DESCRIPTION OF THE INVENTION

The fluid of the invention is used in the same way as conventional antifreeze coolants based on ethylene glycol. The same types of corrosion inhibitors, antioxidants, antifoam agents, lubricants, leak stoppers and other additives that are conventionally used in glycol-based antifreezes are also useful and effective in fluids based on propylene glycol monomethyl ether; hence, they need not be enumerated or further discussed here.

The rotary engine used in the tests described herein was that of a 1972 Mazda R-100 coupe weighing 2040 lb. It had a two-rotor, water-cooled Wankel engine of 9.4:1 compression ratio and was rated at 110 brake horsepower at 7000 r.p.m. The cooling system had a capacity of 7.5 qt., including the heater. The water pump had a capacity of 30 g.p.m., the thermostat was fully open at 194°F. and the radiator was of the corrugated fin type with 51 sq. ft. of core area. The pressure cap opened at 12.8 p.s.i.g.

Thermocouples were installed at critical areas in the top, middle and bottom of each rotor housing about 0.050 inch from the inner wall of the housing. Since the hottest spots were found to be the combustion sides of the two rotor housings, only the readings at these points are included herein.

Since the differences in cooling efficiencies of various coolant fluids become significant only under relatively severe conditions, the data shown in Tables I and II were obtained at road speeds of 70 and 80 m.p.h. and with coolant antifreeze concentrations up to 70%. The tables also include data taken in a peak acceleration test wherein the car was accelerated with wide-open throttle from a standing start to 7000 r.p.m. in third gear. The reported temperatures are the average of two runs made in opposite directions on the test course.

TABLE I

| Coolant | Conc., Vol. % | Rear Rotor Housing Housing Temp., °F. | | |
|---|---|---|---|---|
| | | 70 MPH | 80 MPH | Acceleration |
| Water | — | 264 | 293 | 349 |
| Ethylene Glycol | 34 | 283 | 310 | 367 |
| " | 50 | 301 | 333 | 393 |
| " | 70 | 316 | 353 | 419 |
| Methoxypropanol | 34 | 280 | 306 | 364 |
| " | 50 | 288 | 315 | 376 |
| " | 70 | 298 | 326 | 390 |

TABLE II

| Coolant | Conc., Vol. % | Front Rotor Housing Housing Temp., °F. | | |
|---|---|---|---|---|
| | | 70 MPH | 80 MPH | Acceleration |
| Water | | 261 | 282 | 328 |
| Ethylene Glycol | 34 | 287 | 310 | 353 |
| " | 50 | 309 | 334 | 383 |
| " | 70 | 329 | 359 | 409 |
| Methoxypropanol | 34 | 281 | 300 | 344 |
| " | 50 | 287 | 306 | 351 |
| " | 70 | 297 | 318 | 363 |

While methoxypropanol used in the above tests was the commercial material consisting essentially of 1-methoxy-2-propanol, the isomeric 2-methoxy-1-propanol is quite similar in properties and gives essentially equivalent results.

I claim:

1. The process of cooling a liquid-cooled rotary internal combustion engine comprising circulating an aqueous solution of 2-methoxypropanol in the coolant passages of said engine.

2. The process of cooling a liquid-cooled rotary internal combustion engine comprising circulating in the cooling system thereof an aqueous solution of propylene glycol monomethyl ether containing about 25–70% by volume of the ether.

* * * * *